(12) United States Patent
Brun et al.

(10) Patent No.: US 10,527,605 B2
(45) Date of Patent: Jan. 7, 2020

(54) BLOOD CONDITION ANALYZING DEVICE, BLOOD CONDITION ANALYZING SYSTEM, AND BLOOD CONDITION ANALYZING PROGRAM

(71) Applicant: Sony Corporation, Tokyo (JP)

(72) Inventors: Marcaurele Brun, Tokyo (JP); Yoshihito Hayashi, Chiba (JP); Ludovic Keiser, Gentilly (FR)

(73) Assignee: Sony Corporation, Tokyo (JP)

( * ) Notice: Subject to any disclaimer, the term of this patent is extended or adjusted under 35 U.S.C. 154(b) by 655 days.

(21) Appl. No.: 14/772,483

(22) PCT Filed: Feb. 20, 2014

(86) PCT No.: PCT/JP2014/054002
§ 371 (c)(1),
(2) Date: Sep. 3, 2015

(87) PCT Pub. No.: WO2014/141845
PCT Pub. Date: Sep. 18, 2014

(65) Prior Publication Data
US 2016/0011170 A1 Jan. 14, 2016

(30) Foreign Application Priority Data

Mar. 13, 2013 (JP) .................. 2013-050822
Dec. 20, 2013 (JP) .................. 2013-263944

(51) Int. Cl.
*G01N 33/49* (2006.01)
*G01N 27/22* (2006.01)
*G01N 27/06* (2006.01)

(52) U.S. Cl.
CPC .......... *G01N 33/49* (2013.01); *G01N 27/06* (2013.01); *G01N 27/221* (2013.01)

(58) Field of Classification Search
CPC .................................................. G01N 33/49
USPC ........................................................ 702/19
See application file for complete search history.

(56) References Cited

U.S. PATENT DOCUMENTS

| 8,132,446 B2 | 3/2012 | Hayashi |
| 8,478,546 B2 | 7/2013 | Katsumoto et al. |
| 9,097,635 B2 | 8/2015 | Hayashi |
| 9,915,599 B2 | 3/2018 | Brun et al. |
| 9,952,168 B2 | 4/2018 | Brun et al. |
| 2009/0293595 A1 | 12/2009 | Hayashi |
| 2010/0136606 A1 | 6/2010 | Katsumoto et al. |
| 2012/0035450 A1 | 2/2012 | Hayashi |
| 2012/0084022 A1 | 4/2012 | Giovangrandi et al. |
| 2012/0137753 A1 | 6/2012 | Hayashi |
| 2012/0238026 A1 | 9/2012 | Hayashi et al. |
| 2015/0323480 A1 | 11/2015 | Brun et al. |
| 2015/0346125 A1 | 12/2015 | Hayashi et al. |
| 2015/0377763 A1 | 12/2015 | Brun et al. |
| 2016/0018346 A1 | 1/2016 | Hayashi et al. |
| 2016/0025610 A1 | 1/2016 | Katsumoto et al. |
| 2016/0282366 A1 | 9/2016 | Hayashi et al. |
| 2016/0299124 A1 | 10/2016 | Brun et al. |
| 2018/0202955 A1 | 7/2018 | Brun et al. |

FOREIGN PATENT DOCUMENTS

| EP | 2 375 244 A1 | 10/2011 |
| EP | 2 500 726 A1 | 9/2012 |
| JP | 2010-181400 A | 8/2010 |
| JP | 2011-112497 A | 6/2011 |
| JP | 2012-194087 A | 10/2012 |
| WO | WO 2014/141845 | 9/2014 |

OTHER PUBLICATIONS

U.S. Appl. No. 14/772,550, filed Sep. 3, 2015, Hayashi et al.
U.S. Appl. No. 14/777,906, filed Sep. 17, 2015, Brun et al.
U.S. Appl. No. 14/778,277, filed Sep. 18, 2015, Hayashi et al.
Irimajiri et al., Rapid Report—Dielectric monitoring of rouleaux formation in human whole blood: a feasibility study. Biochimica et Biophysica Acta , vol. 1290, 1996: pp. 207-209.
Irimajiri et al., Zenketsu no yuden kyodo kara mita sekkekkyu gyoshu (Renzen Keisei). Biotechnology, vol. 78, No. 5, 2000: pp. 162-165.
U.S. Appl. No. 12/472,630, filed May 27, 2009, Hayashi.
U.S. Appl. No. 12/733,031, filed Feb. 3, 2010, Katsumoto et al.
U.S. Appl. No. 13/371,881, filed Feb. 13, 2012, Hayashi.
U.S. Appl. No. 14/760,238, filed Jul. 10, 2015, Hayashi et al.
International Search Report and Written Opinion and English translation thereof dated Mar. 25, 2014 in connection with International Application No. PCT/JP2014/054002.
International Preliminary Report on Patentability and English translation thereof dated Sep. 24, 2015 in connection with International Application No. PCT/JP2014/054002.
U.S. Appl. No. 15/920,911, filed Mar. 14, 2018, Brun et al.
Japanese Office Action dated Aug. 20, 2019 in connection with Japanese Application No. 2018-195142, and English translation thereof.
Chinese Office Action dated Jul. 2, 2019 in connection with Chinese Application No. 2014800125289, and English translation thereof.

*Primary Examiner* — Jerry Lin
(74) *Attorney, Agent, or Firm* — Wolf, Greenfield & Sacks, P.C.

(57) ABSTRACT

There is provided a blood condition analyzing device including: an extraction unit configured to use temporal change data of an electrical characteristic of blood at an arbitrary frequency to extract a feature of the data; and a blood condition evaluation unit configured to evaluate a condition change of blood from a feature extracted in the extraction unit.

16 Claims, 14 Drawing Sheets

BLOOD CONDITION ANALYZING DEVICE, BLOOD CONDITION ANALYZING SYSTEM, AND BLOOD CONDITION ANALYZING PROGRAM

CROSS REFERENCE TO RELATED APPLICATIONS

This application claims the benefit under 35 U.S.C. § 371 as a U.S. National Stage Entry of International Application No. PCT/JP2014/054002, filed in the Japanese Patent Office as a Receiving Office on Feb. 20, 2014, which claims priority to Japanese Patent Application Number JP2013-263944, filed in the Japanese Patent Office on Dec. 20, 2013 and Japanese Patent Application Number JP2013-050822, filed in the Japanese Patent Office on Mar. 13, 2013, each of which is hereby incorporated by reference in its entirety.

TECHNICAL FIELD

The present technology relates to a blood condition analyzing device. More specifically, the present technology relates to a blood condition analyzing device, a blood condition analyzing system, and a blood condition analyzing program capable of automatically analyzing the condition change of blood from the temporal change of the electrical characteristics of the blood.

BACKGROUND ART

A technology in which the electrical characteristics of a blood sample are measured and the condition of the blood is determined from the measurement results has been conventionally used. For example, Patent Literature 1 discloses a technology in which information on blood coagulation is acquired from the dielectric constant of blood, and describes "a blood coagulation system analyzing device including a pair of electrodes, applying means for applying an AC voltage to the pair of electrodes at prescribed time intervals, measuring means for measuring the dielectric constant of blood disposed between the pair of electrodes, and analyzing means for analyzing the degree of working of a blood coagulation system using the dielectric constant of blood measured at the time intervals after the anticoagulant effect working on the blood is removed."

Thus far, mechanical indices such as viscoelasticity have been used to analyze the condition of blood coagulation. However, by measuring electrical characteristics such as the dielectric constant of blood as in Patent Literature 1 above, the diagnosis of blood coagulation can be made earlier in a stage before a mechanical change such as a viscosity change occurs. Therefore, it is possible to select more appropriate therapeutic methods and medication methods earlier for patients or others with a risk of thrombosis etc.

Furthermore, for example, Patent Literature 2 discloses a blood cell analyzing device capable of evaluating effects and side effects of a drug in a short time by including a measuring unit that measures the complex dielectric constant spectrum of a suspension containing one or a plurality of blood cells and a detection unit that calculates the dielectric variable and/or the electrical property value of the suspension on the basis of the complex dielectric constant spectrum measured in the measuring unit and uses the calculated value to detect a condition change of the blood cell accompanying drug administration.

CITATION LIST

Patent Literature

Patent Literature 1: JP 2010-181400A
Patent Literature 2: JP 2011-112497A

SUMMARY OF INVENTION

Technical Problem

As described above, these days the development of devices etc. in which the electrical characteristics of a blood sample are measured and the condition of the blood is determined from the measurement results is advanced. If these devices are realized, rapid and accurate diagnoses can be actually made in medical sites; thus, high expectations are placed on them.

However, in devices so far developed, the determination of the condition of blood has been performed in a way that a user extracts a feature of a blood sample from the measured value of the electrical characteristics of the blood sample and the user compares the feature to a criterion value set by the user or the like. Hence, the determination has often been greatly influenced by the skill or experience value of the user, and there has been a case where it takes a large amount of time to complete determination.

Thus, a main object of the present technology is to provide a technology capable of automatically analyzing the condition change of blood from the temporal change of the electrical characteristics of the blood.

Solution to Problem

According to the present technology, there is provided a blood condition analyzing device including: an extraction unit configured to use temporal change data of an electrical characteristic of blood at an arbitrary frequency to extract a feature of the data; and a blood condition evaluation unit configured to evaluate a condition change of blood from a feature extracted in the extraction unit.

In the blood condition analyzing device according to the present technology, the extraction of a feature from the temporal change data and the evaluation of the blood condition based on the feature are automatically performed in the device.

The blood condition analyzing device according to the present technology may further include an extraction criterion setting unit configured to set an extraction criterion in the extraction unit.

The blood condition analyzing device according to the present technology may further include a denoising unit configured to remove noise of the temporal change data of the electrical characteristic.

The blood condition analyzing device according to the present technology may further include a reliability evaluation unit configured to evaluate reliability of the temporal change data of the electrical characteristic.

The blood condition analyzing device according to the present technology may further include a measuring unit configured to measure an electrical characteristic of blood at an arbitrary frequency over time.

The blood condition analyzing device according to the present technology may further include an extraction result storage unit configured to store an extraction result in the extraction unit.

The blood condition analyzing device according to the present technology may further include a blood condition evaluation storage unit configured to store an evaluation result in the blood condition evaluation unit.

The blood condition analyzing device according to the present technology may further include a measurement result storage unit configured to store a measurement result in the measuring unit.

Next, according to the present technology, there is provide a blood condition analyzing system including: an electrical characteristic measuring device including a measuring unit configured to measure an electrical characteristic of blood at an arbitrary frequency over time; and a blood condition analyzing device including an extraction unit configured to use temporal change data of an electrical characteristic of blood at an arbitrary frequency to extract a feature of the data and a blood condition evaluation unit configured to evaluate a condition change of blood from a feature extracted in the extraction unit.

The blood condition analyzing system according to the present technology may further include a server including an information storage unit configured to store a measurement result in the electrical characteristic measuring device and/or an analysis result in the blood condition analyzing device.

In this case, the server may be connected to the electrical characteristic measuring device and/or the blood condition analyzing device via a network.

In addition, according to the present technology, there is provided a blood condition analyzing method for performing: an extraction process of using temporal change data of an electrical characteristic of blood at an arbitrary frequency to extract a feature of the data; and a blood condition evaluation process of evaluating a condition change of blood from a feature extracted in the extraction process.

In addition, according to the present technology, there is provided a blood condition analyzing program for causing a computer to execute: an extraction function of using temporal change data of an electrical characteristic of blood at an arbitrary frequency to extract a feature of the data; and a blood condition evaluation function of evaluating a condition change of blood from a feature extracted in the extraction function.

Advantageous Effects of Invention

According to the present technology, the extraction of a feature from temporal change data and the evaluation of the blood condition based on the feature which conventionally a user has been performed are automatically performed in the device; therefore, more accurate and rapid analysis is possible. The effects described herein are not necessarily limitative ones, and any effect described in the present disclosure is possible.

DESCRIPTION OF EMBODIMENTS

Figure 1:
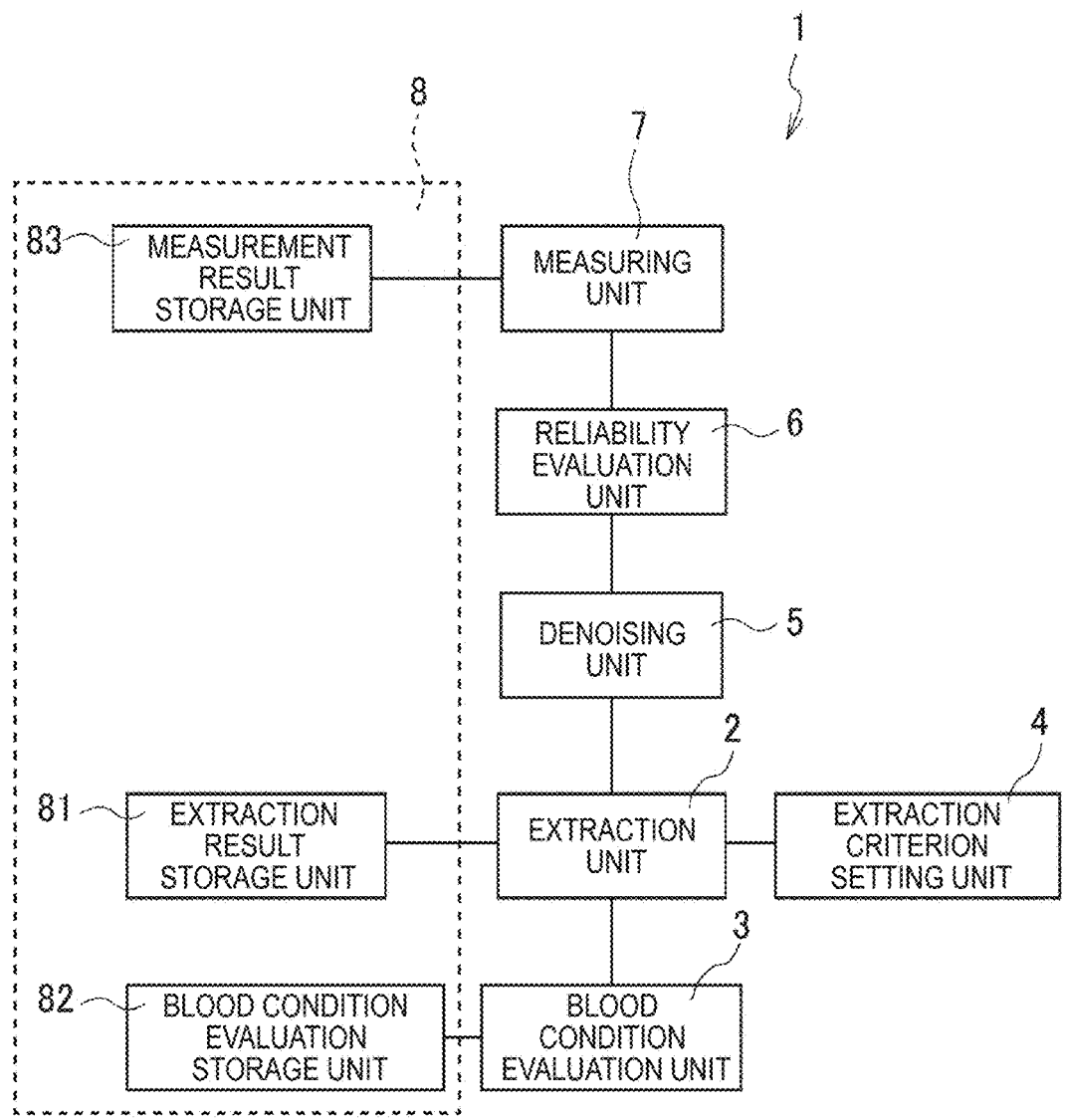
FIG. 1 is a schematic conceptual diagram schematically showing the concept of a blood condition analyzing device 1 according to the present technology.

Hereinbelow, preferred embodiments for carrying out the present technology are described with reference to the drawings. The embodiments described below are examples of the typical embodiments of the present technology, and the scope of the present technology is not construed as being limited by the embodiments. The description is given in the following order:

1. Blood condition analyzing device 1
(1) Reliability evaluation unit 6
(2) Denoising unit 5
(3) Extraction unit 2 and Blood condition evaluation unit 3
(4) Extraction criterion setting unit 4
(5) Measuring unit 7
(6) Storage unit 8
(7) Blood sample 2. Blood condition analyzing system 10
(1) Electrical characteristic measuring device 101

(2) Blood condition analyzing device 1
(3) Server 102
(4) Display unit 103
(5) User interface 104
3. Blood condition analyzing method
(1) Extraction process I
(2) Blood condition evaluation process II
(3) Extraction criterion setting process III
(4) Denoising process IV
(5) Reliability evaluation process V
(6) Measuring process VI
(7) Storage process VII
4. Blood condition analyzing program
1. Blood Condition Analyzing Device 1

FIG. 1 is a schematic conceptual diagram schematically showing the concept of a blood condition analyzing device 1 according to the present technology. The blood condition analyzing device 1 according to the present technology includes, in terms of broad categories, at least an extraction unit 2 and a blood condition evaluation unit 3. The blood condition analyzing device 1 may include, as necessary, an extraction criterion setting unit 4, a denoising unit 5, a reliability evaluation unit 6, a measuring unit 7, a storage unit 8, etc. Each component will now be described in detail. In the following, the description is given in line with the sequence of analysis.

(1) Reliability Evaluation Unit 6

In the reliability evaluation unit 6, the reliability of the temporal change data of electrical characteristics is evaluated. In the blood condition analyzing device 1 according to the present technology, the reliability evaluation unit 6 is not essential, but is preferably included in order to improve analysis precision more.

In the blood condition analyzing device 1 according to the present technology, as specific reliability evaluation methods performed in the reliability evaluation unit 6, one or more known methods may be freely selected for use to the extent that the effect of the present technology is not impaired. For example, the reliability of the temporal change data of electrical characteristics can be evaluated by finding the signal-to-noise ratio (SNR).

In the present technology, also the method for calculating the SNR is not particularly limited, and one or more known methods may be freely selected for use. For example, calculation can be made in the following manner.

(a) Calculation of the Noise Amount (N)

The noise amount (N) can be calculated by, for example, freely combining one or more of the methods of (i) to (v) below. Of these, the method of (i) below is preferably used for calculation in the present technology.

(i) As shown in Mathematical Formula (1) below, the sum of the absolute value of the difference between the amplitude values of two adjacent data is taken as the noise amount (N).

[Math. 1]

$$N = \sum_{2 \le t \le tmax} \mathrm{abs}(A(t) - A(t-1)) \tag{1}$$

(ii) The proportion of the cases where the difference between adjacent amplitude values is larger than the fraction of the total amplitude is taken as the noise amount (N).

(iii) The proportion of the cases where the difference between adjacent amplitude values fluctuates between plus and minus is taken as the noise amount (N).

(iv) The average of the difference between adjacent amplitude values is taken as the noise amount (N).

(v) The sum or average value of the difference of each point to a smooth curve is taken as the noise amount (N).

(b) Calculation of the Signal Amount (S)

The signal amount (S) can be calculated by, for example, freely combining one or more of the methods of (i) to (v) below. Of these, the method of (i) below is preferably used for calculation in the present technology.

(i) As shown in Mathematical Formula (2) below, the change in the total amplitude value is taken as the signal amount (S).

[Math. 2]

$$S = \max_{1 \le t \le tmax} A(t) - \min_{1 \le t \le tmax} A(t) \tag{2}$$

(ii) The proportion of the cases where the difference between adjacent amplitude values is smaller than the fraction of the total amplitude is taken as the signal amount (S). This method is used in combination with the method for calculating the noise amount (ii).

(iii) The proportion of the cases where the difference between adjacent amplitude values does not fluctuate between plus and minus is taken as the signal amount (S). This method is used in combination with the method for calculating the noise amount (iii).

(iv) The maximum value of amplitude is taken as the signal amount (S).

(v) The average value of amplitude is taken as the signal amount (S).

(c) Calculation of the SNR

For the noise amount (N) and the signal amount (S) calculated in the above, the SNR is calculated using Mathematical Formula (3) below.

[Math. 3]

$$SNR = \frac{S}{N} \tag{3}$$

Figure 2:
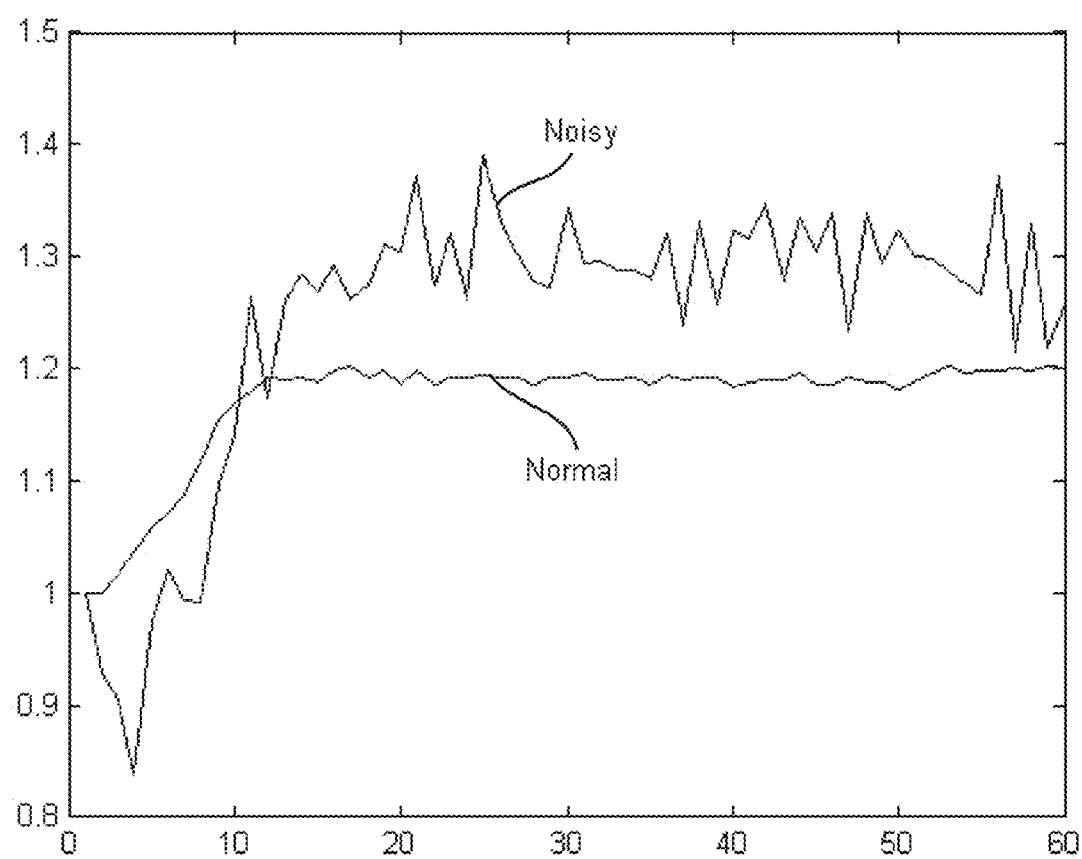
FIG. 2 is a drawing-substitute graph showing examples of data with a large amount of noise (Noisy) and normal data (Normal) when the dielectric constant of blood is measured over time.

The methods for calculating the noise amount (N) (i) to (v) and the methods for calculating the signal amount (S) (i) to (v) mentioned above can be freely combined in accordance with the objective. For example, when the SNR is calculated using the combinations of Table 1 below for data with a large amount of noise (Noisy) and normal data (Normal) illustrated in FIG. 2 when the dielectric constant of blood is measured over time, Table 2 below is obtained.

TABLE 1

| SNR method name | Noise evaluation | Signal evaluation | Method |
| --- | --- | --- | --- |
| SNR_1 | (i) | (i) | divide |
| SNR_2 | (i) | (iv) | divide |
| SNR_3 | (i) | (v) | divide |
| SNR_4 | (ii) | (ii) | divide |

TABLE 2

|       | Noisy  | Normal |
|-------|--------|--------|
| SNR_1 | 0.1791 | 0.5004 |
| SNR_2 | 0.4505 | 2.9605 |
| SNR_3 | 0.403  | 2.8853 |
| SNR_4 | 0.2527 | 2.337  |

(2) Denoising Unit 5

In the denoising unit 5, the noise of the temporal change data of electrical characteristics is removed. In the blood condition analyzing device 1 according to the present technology, the denoising unit 5 is not essential, but is preferably included in order to improve analysis precision more.

In the blood condition analyzing device 1 according to the present technology, as specific denoising methods performed in the denoising unit 5, one or more known methods may be freely selected for use to the extent that the effect of the present technology is not impaired. For example, the methods illustrated in (a) and (b) below may be given.

(a) Local Smoothing

Figure 3:
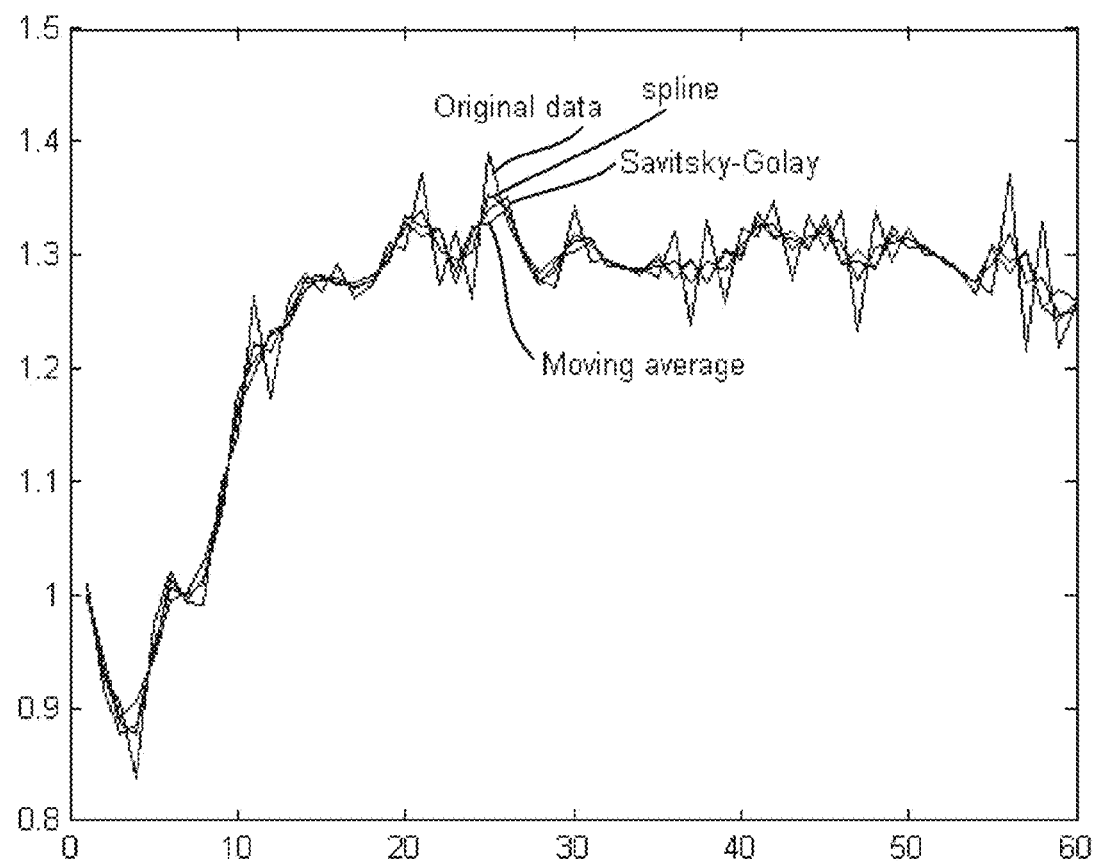
FIG. 3 is a drawing-substitute graph showing examples in which, for data of the dielectric constant of blood measured over time, denoising is performed using the moving average method, Savitsky-Golay approximation, and spline approximation.

The smoothing of data can be made using, for example, the moving average method, Savitsky-Golay approximation, or spline approximation, or a method in which these are combined. When these methods are used, it is possible to remove noise while preventing influence on the signal value. Examples in which denoising is performed using these methods are shown in FIG. 3.

(b) Model Fitting

Figure 4:
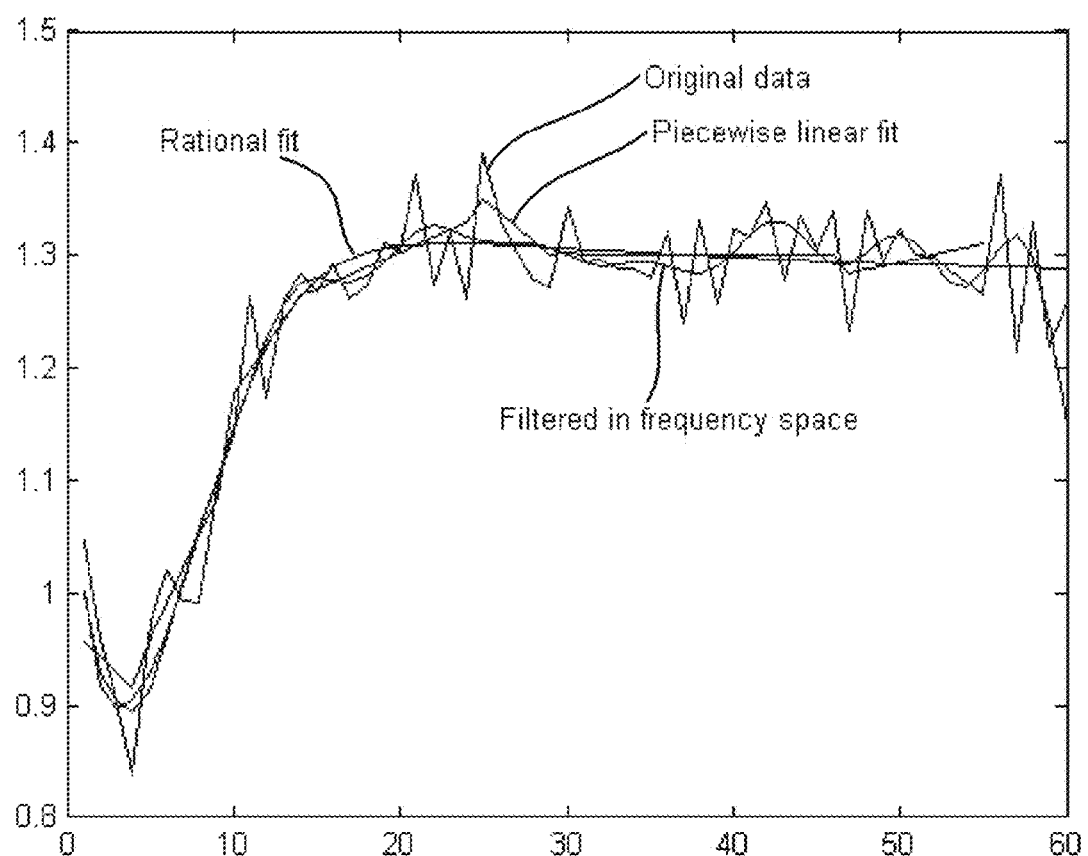
FIG. 4 is a drawing-substitute graph showing, for data of the dielectric constant of blood measured over time, an example in which denoising is performed using Mathematical Formula (4) and an example in which denoising is performed using Fourier transformation.

FIG. 4 is a drawing-substitute graph showing an example in which denoising is performed using Mathematical Formula (4) below and an example in which denoising is performed using Fourier transformation. It is also possible to perform similar denoising using similar functions other than Mathematical Formula (4) or transformation methods similar to each transformation. It is also possible to perform denoising by combining these methods. FIG. 4 is a graph when n, m=5.

[Math. 4]

$$F(x) = \frac{a + cx + ex^2 + gx^3 + ix^4 + \ldots + rx^n}{b + dx + fx^2 + hx^3 + jx^4 + \ldots + sx^m} \quad (4)$$

s: fitting coefficient
n, m: integer (3) Extraction Unit 2 and Blood Condition Evaluation Unit 3

In the extraction unit 2, the temporal change data of the electrical characteristics of blood at an arbitrary frequency are used to extract a feature of the data. In the blood condition evaluation unit 3, the condition change of blood is evaluated from the feature extracted in the extraction unit 2.

For the temporal change data of electrical characteristics, when an external electrical characteristic measuring device is provided or the blood condition analyzing device 1 according to the present technology is provided with the measuring unit 7 described later, the raw data measured in the measuring unit 7 can be used as they are. Alternatively, when the blood condition analyzing device 1 according to the present technology includes the denoising unit 5 described above, it is possible to use data in which noise is removed from the raw data measured in the external electrical characteristic measuring device or the measuring unit 7. Furthermore, it is also possible to use data in which noise is removed from the raw data measured in the external electrical characteristic measuring device or the measuring unit 7 using an external device having a denoising function.

As the electrical characteristics of blood that can be analyzed by the blood condition analyzing device 1 according to the present technology, for example, dielectric constant, impedance, admittance, capacitance, conductance, electrical conductivity, phase angle, an amount obtained by transforming these in electrical quantity, etc. may be given.

The condition of blood that can be analyzed by the blood condition analyzing device 1 according to the present technology is not particularly limited to the extent that it is a phenomenon in which a temporal change in the electrical characteristics of blood is seen due to a condition change, and various condition changes can be analyzed and evaluated. For example, the coagulation of blood (blood coagulation), fibrin formation, fibrin clot formation, blood clot formation, blood platelet coagulation, the rouleaux formation of red blood cells, the aggregation of blood, the sedimentation of red blood cells (erythrocyte sedimentation), blood clot retraction, hemolysis such as fibrinolysis, fibrinolysis, etc. may be given.

In the extraction unit 2 and the blood condition evaluation unit 3 of the blood condition analyzing device 1 according to the present technology, the method for extracting a feature of the temporal change data of the electrical characteristics of blood and the blood condition evaluation method are not particularly limited, and one or more mathematical methods may be used. The extraction method and blood condition evaluation will now be described using specific examples. Embodiments 1 to 5 illustrated below describe typical examples of the extraction method and the blood condition evaluation method that can be used in the present technology, and the scope of the present technology is not construed as being limited by these.

(a) Embodiment 1

Embodiment 1 is an example in which the temporal change data of the electrical characteristics of blood are linearly approximated using the linear approximation method, features are extracted from the obtained line segments, and the blood condition is evaluated from the extracted feature points.

a. First, the temporal change data of electrical characteristics are approximated by linear approximation so that the distance from each approximated datum is statistically smaller than data noise. Specifically, the approximation is performed as follows.

(i) An approximate straight line of four or more data A(t) is created from time t0. More specifically, a and b whereby Mathematical Formula (5) below is at the minimum are calculated (use of the least squares method).

[Math. 5]

$$\sum_{t0}^{t0+4} [(a*t + b) - A(t)]^2 \quad (5)$$

(ii) In the case where the error value between the approximated data and the raw data is smaller than noise data, an approximate straight line can be created. Although the function used is not particularly limited, Mathematical Formula (7) below can be used when Mathematical Formula (6) below holds, for example.

[Math. 6]

$$\sum_{t0}^{t0+length} \text{abs}((a*t+b) - A(t))/length \leq \sum_{2 \leq t \leq tmax} \text{abs}(A(t) - A(t-1))/numel(A) \quad (6)$$

[Math. 7]

$$length = length + 1 \quad (7)$$

(iii) In the case where Mathematical Formula (6) above does not hold, the flow returns to the step of (i) again and time t0 is set in the manner of Mathematical Formula (8) below.

[Math. 8]

$$t0 = t0 + length \quad (8)$$

Figure 5:
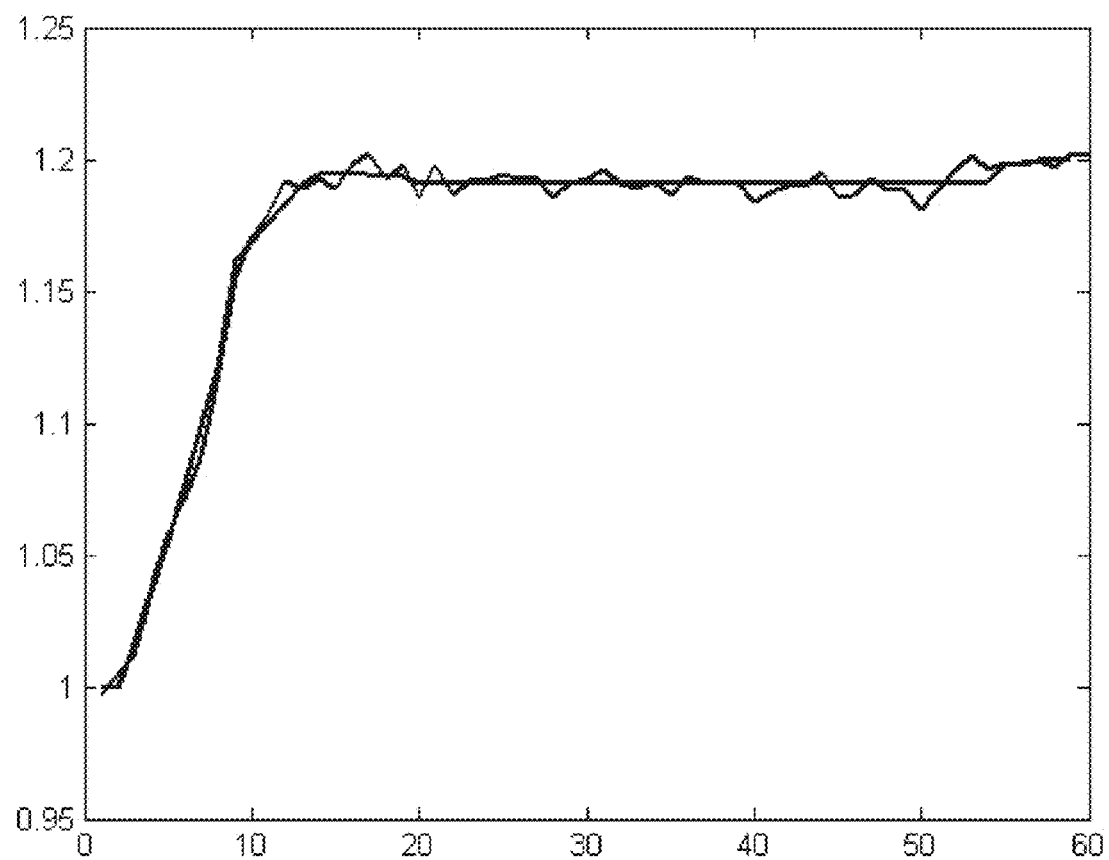
FIG. 5 is a drawing-substitute graph showing an example in which the linear approximation method of Embodiment 1 is used for data of the dielectric constant of blood measured over time.

(iv) An example in which the processing of (i) to (iii) above is performed on the data of the dielectric constant of blood measured over time is shown in FIG. 5. The method of linear approximation is not limited to the method described above, and known methods may be freely selected for use. As another example of linear approximation, it is possible to minimize the error between the approximate straight line and the original data in a state where the minimum value of the line segment is kept.

b. Next, specific line segments are selected from the obtained line segments by the following method.

(i) Some lines with the maximum slope are selected. As the method for specifying the "some lines," for example, a method in which some line segments are selected so that at least 70 percent of the total fluctuation range is covered is given. In the example shown in FIG. 6, only line segments that come under the condition that the origin be smaller than 1 and the slope be half or more of the largest slope are selected.

Figure 6:
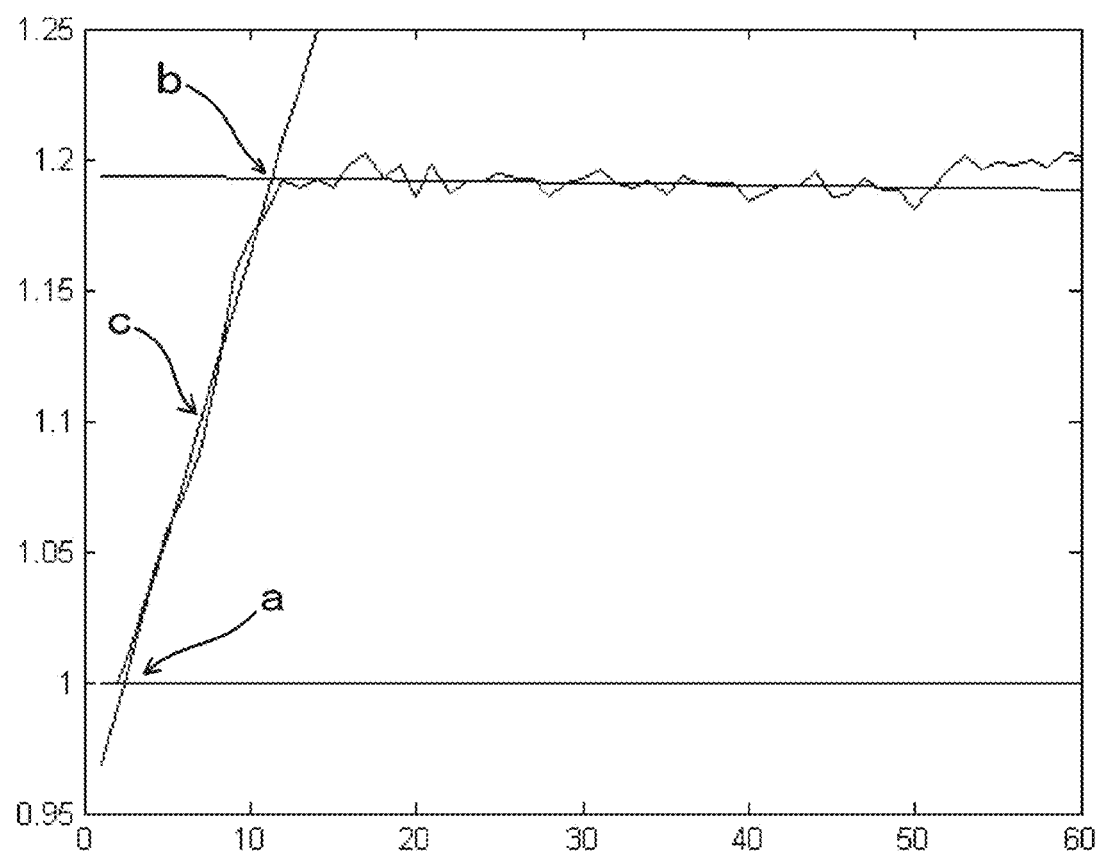
FIG. 6 is a drawing-substitute graph showing an example in which, for data of the dielectric constant of blood measured over time, the linear approximation of Embodiment 1 is performed and the blood condition is evaluated from the obtained line segments.

(ii) Similarly, some lines with the minimum slope are selected. That is, "the most horizontal lines" of which the absolute value of slope is most horizontal are selected. In FIG. 6, line segments that correspond to only times longer than the time corresponding to the line segments selected in the above and line segments of which the origin exists between the origin of the line segments selected in the above and twice this origin are selected.

(iii) Line segments corresponding to times shorter than the time corresponding to the line segments selected with the maximum slope mentioned above are selected.

(iv) A new linear approximation is created by taking the average of slope for each group of line segments selected.

(v) The blood condition can be evaluated from the line segments on which the processing of (i) to (iv) mentioned above has been performed. Specifically, in FIG. 6, the intersection point a indicates the start of coagulation of blood, the intersection point b indicates the end of coagulation of blood, and the line segment c indicates the maximum rate of blood coagulation.

(b) Embodiment 2

Figure 7:
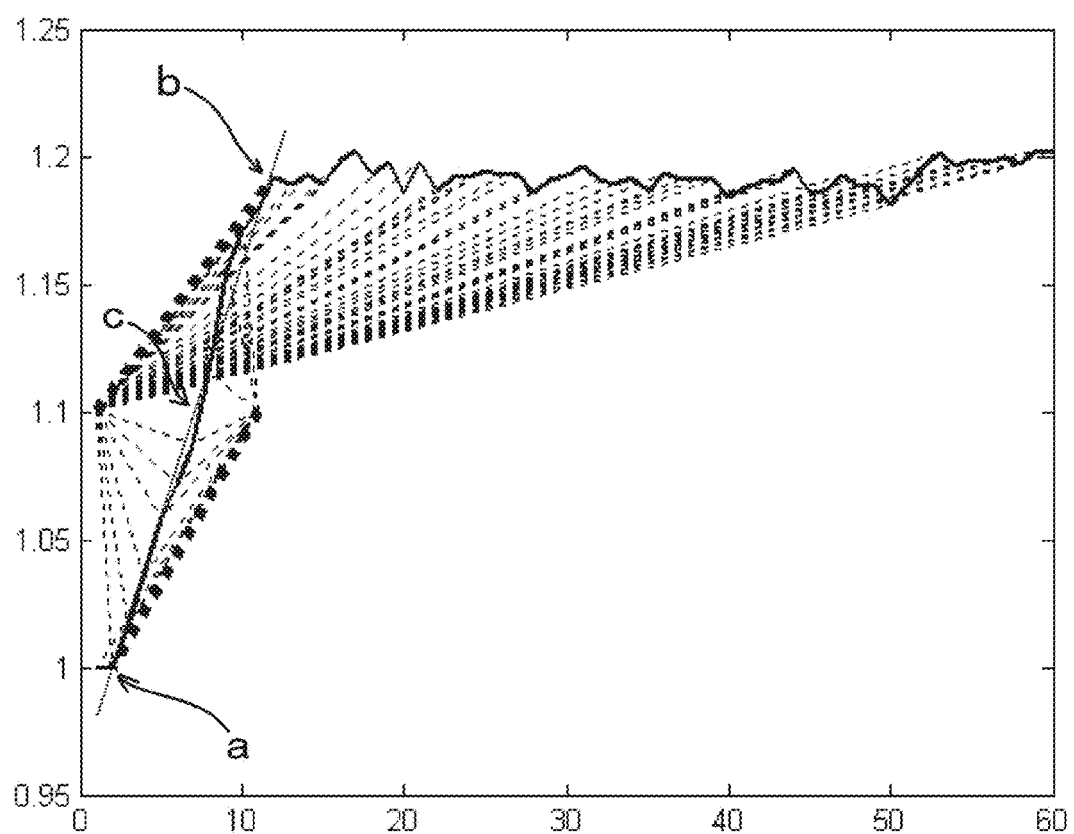
FIG. 7 is a drawing-substitute graph showing an example in which, for data of the dielectric constant of blood measured over time, the linear projection of Embodiment 2 is performed to extract features and the blood condition is evaluated from the obtained features.

Embodiment 2 is an example in which linear projection is performed using the start point and the end point of the temporal change data of the electrical characteristics of blood to extract features and the blood condition is evaluated from the extracted features. Specifically, this is a method of performing the following four steps. A specific example will now be described using FIG. 7.

a. First, the average amplitude M of the minimum value and the maximum value is obtained.

b. Next, line segments are obtained by connecting each datum from the point (1, M). At this time, the line segment with the maximum slope can be evaluated as corresponding to the end of coagulation of blood (see the reference character b in FIG. 7). In order to suppress the influence of noise, it is possible to evaluate the blood condition with consideration of also other line segments etc. in a more complicated manner, instead of evaluating using only the maximum slope, because the slopes of the line segment with the maximum slope and its neighboring line segments almost coincide.

c. Similarly, line segments are obtained by connecting data of t<T from the point (T, M). At this time, the line segment with the maximum slope can be evaluated as corresponding to the start of coagulation of blood (see the reference character a in FIG. 7).

d. The slope between the two points of the coagulation end and the coagulation start obtained in the above can be evaluated as corresponding to the maximum rate of blood coagulation (see the reference character c in FIG. 7).

(c) Embodiment 3

Embodiment 3 is an example in which the feature is defined mathematically, features are extracted from the fitting result of the temporal change data of the electrical characteristics of blood, and the blood condition is evaluated from the extracted features. For example, the maximum value and the minimum value can be extracted using Mathematical Formula (9) below and Mathematical Formula (10) below, which is a differential function of Mathematical Formula (9).

[Math. 9]

$$f(x) = \frac{nd_2 x^2 + nd_1 x + 1}{nd_7 x^2 + nd_6 x + 1} \quad (9)$$

[Math. 10]

$$f'(x) = \quad (10)$$

$$0 \Leftrightarrow \begin{pmatrix} x = \dfrac{nd_2 - nd_7 + \sqrt{\begin{array}{c} nd_1^2 nd_7 - nd_1 nd_2 nd_6 - nd_1 nd_6 nd_7 + \\ nd_2^2 + nd_2 nd_6^2 - 2nd_2 nd_7 + nd_7^2 \end{array}}}{nd_1 nd_7 - nd_2 nd_6} \\ x = -\dfrac{nd_7 - nd_2 + \sqrt{\begin{array}{c} nd_1^2 nd_7 - nd_1 nd_2 nd_6 - nd_1 nd_6 nd_7 + \\ nd_2^2 + nd_2 nd_6^2 - 2nd_2 nd_7 + nd_7^2 \end{array}}}{nd_1 nd_7 - nd_2 nd_6} \end{pmatrix}$$

Similarly, a position where the rate of change is largest can be found using a second differential function of Mathematical Formula (9) above.

Figure 8:
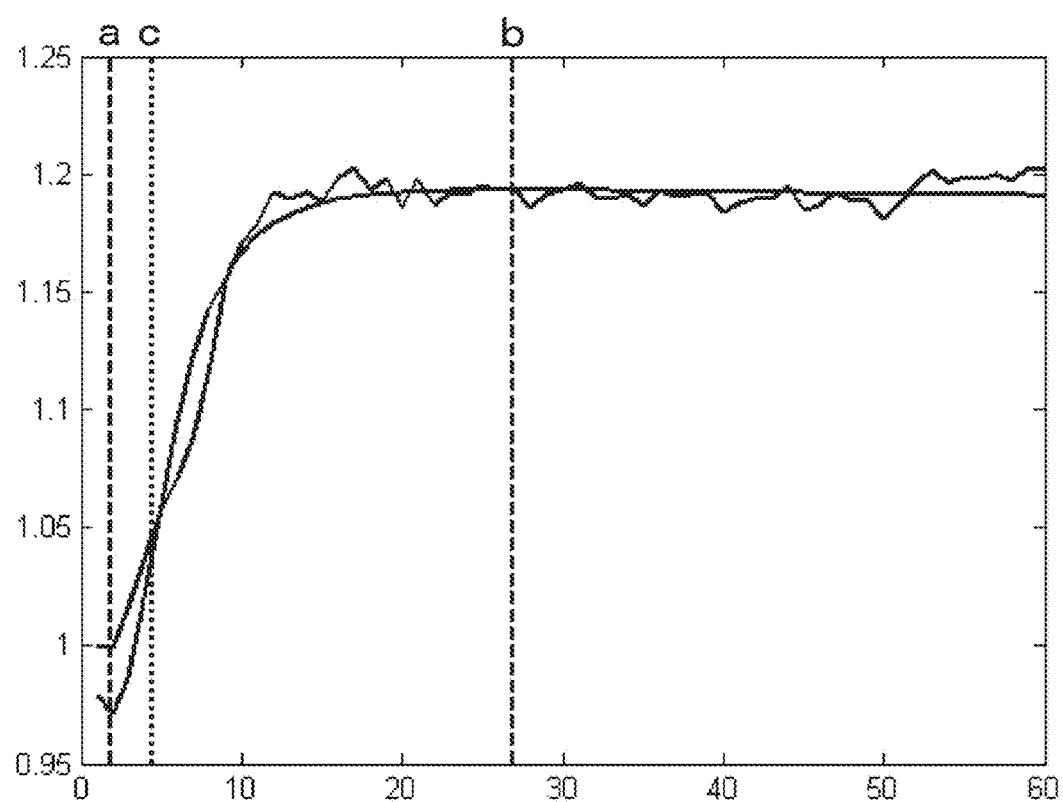
FIG. 8 is a drawing-substitute graph showing an example in which, for data of the dielectric constant of blood measured over time, the method of Embodiment 3 is used to evaluate the blood condition.

In this way, the start time of coagulation of blood (see the reference character a in FIG. 8), the end time of coagulation of blood (see the reference character b in FIG. 8), and the maximum rate of blood coagulation (see the reference character c in FIG. 8) can be obtained.

Figure 9:
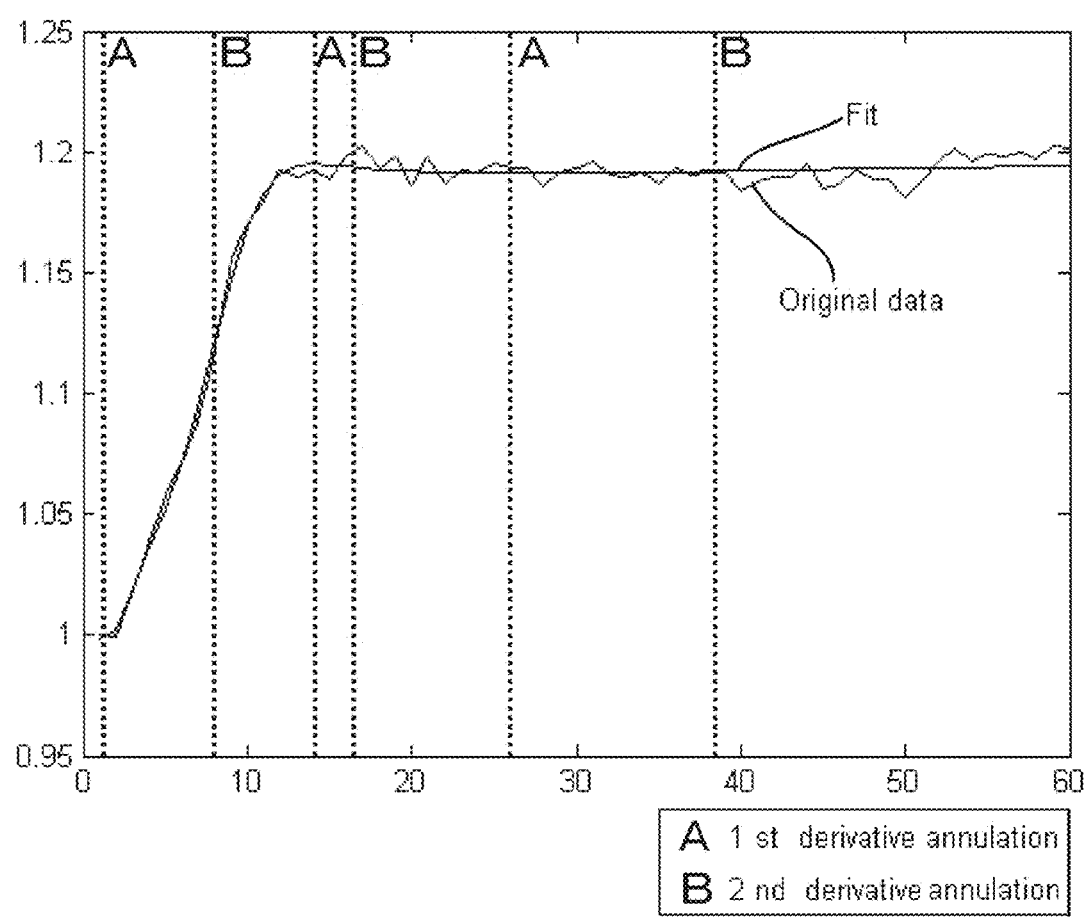
FIG. 9 is a drawing-substitute graph showing an example in which, for data of the dielectric constant of blood measured over time, the method of Embodiment 3 is used to evaluate the blood condition.

Actually, in approximation using higher-order rational functions, good results can be obtained in terms of approximation accuracy. However, in mathematical modeling using different functions, there is a case where different evaluation results are derived as shown in FIG. 9.

(d) Embodiment 4

Embodiment 4 is an example in which, for the temporal change data of the electrical characteristics of blood, features are extracted using a boundary detection algorithm and the blood condition is evaluated from the extracted features. As the boundary detection algorithm, for example, image processing or the like may be used; but not limited to this, known boundary detection algorithms may be used.

Figure 10:
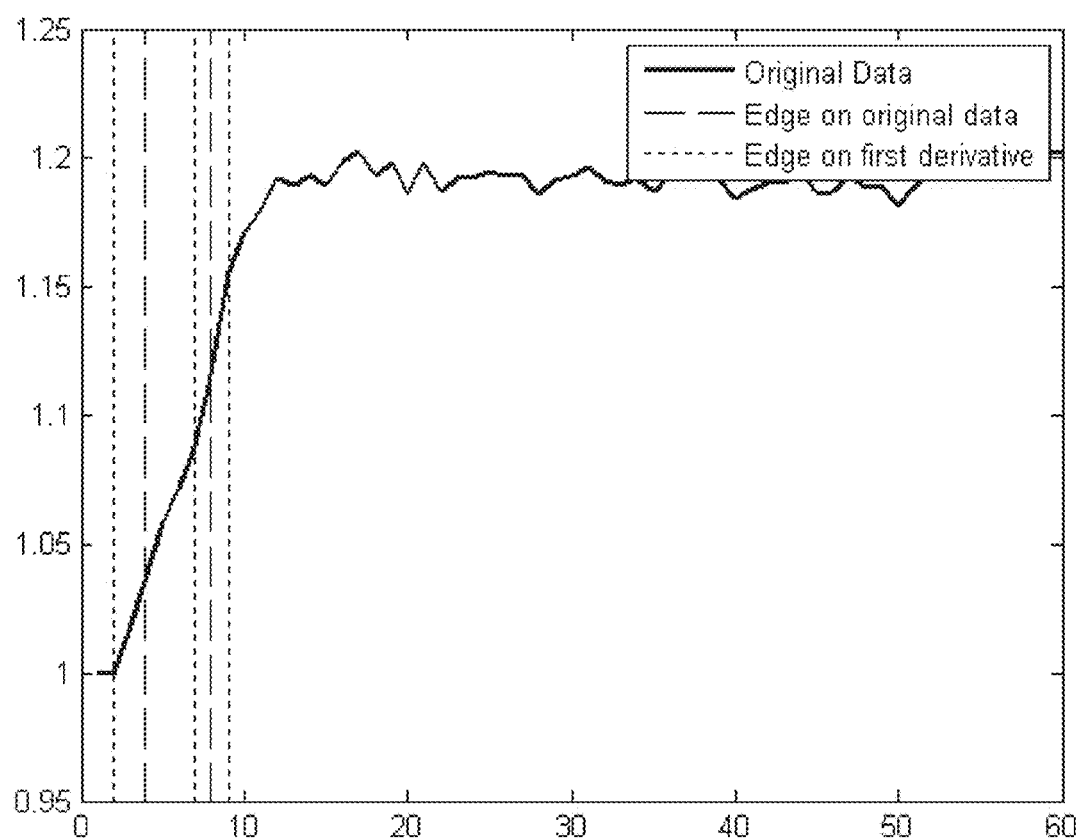
FIG. 10 is a drawing-substitute graph showing an example in which, for data of the dielectric constant of blood measured over time, the method of Embodiment 4 is used to evaluate the blood condition.
Figure 11:
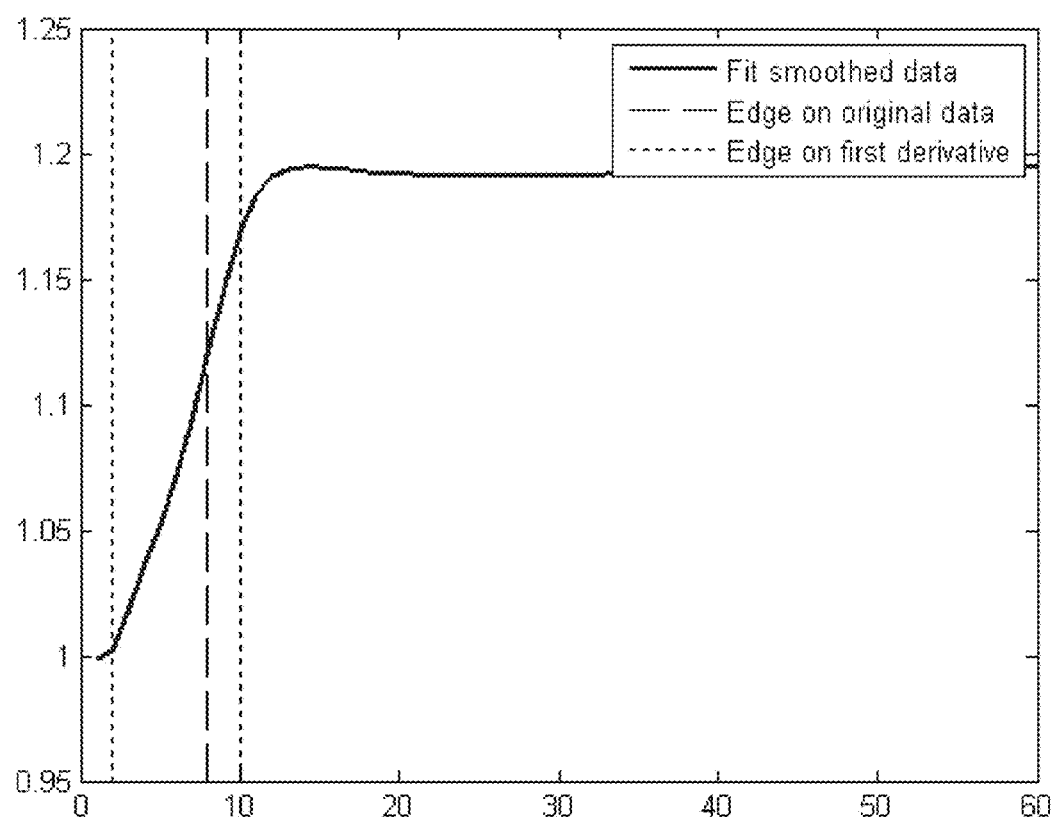
FIG. 11 is a drawing-substitute graph showing an example in which, for data of the dielectric constant of blood measured over time, the method of Embodiment 4 is used to evaluate the blood condition.

When the method of Embodiment 4 is used, features can be extracted for raw data or the first derivative thereof even if noise is included. An example in which features of raw data and the first derivative are extracted by the method of Embodiment 4 is shown in FIG. 10, and an example in which features of data after smoothing are extracted by the method of Embodiment 4 is shown in FIG. 11.

Figure 12:
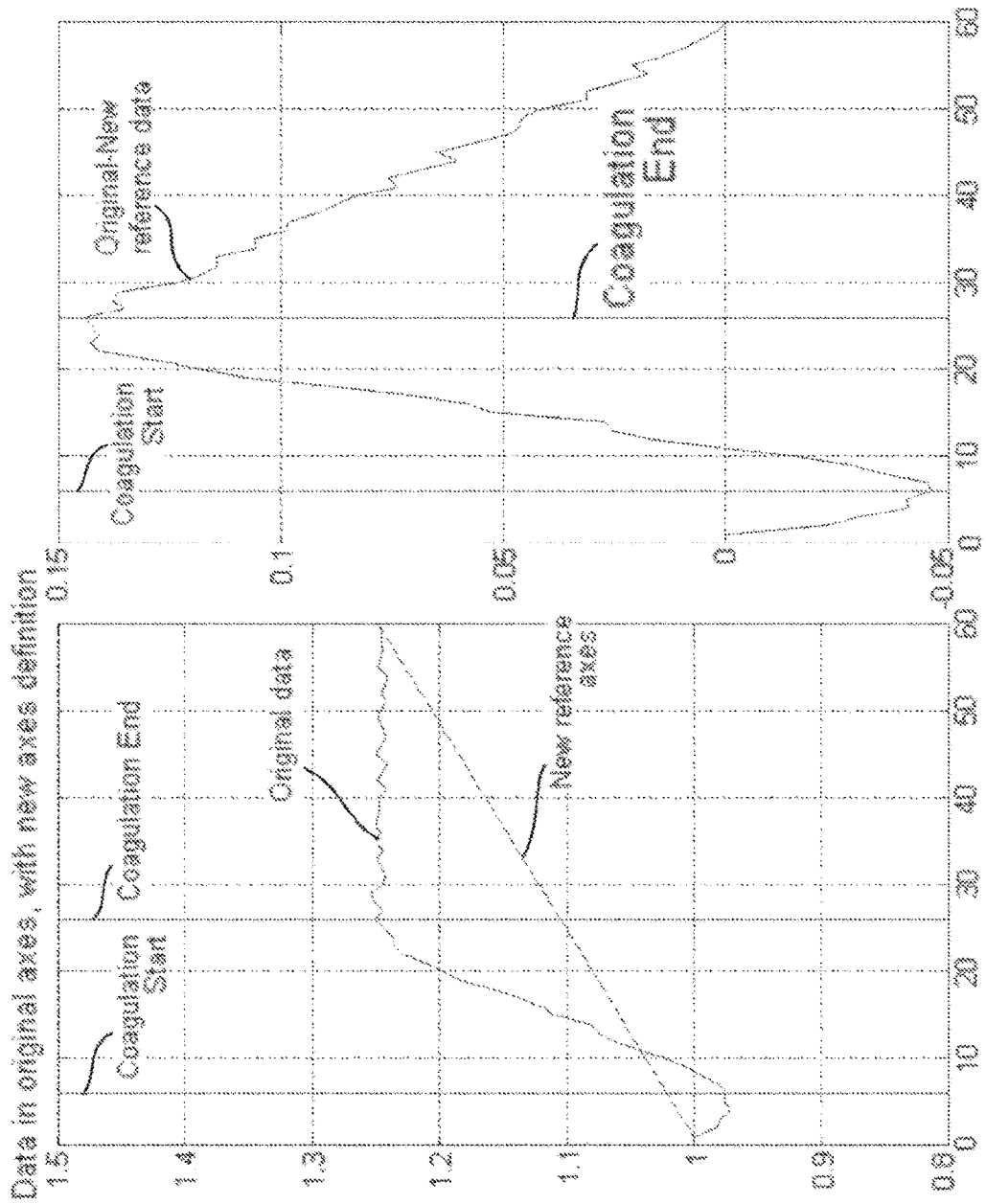
FIG. 12 is a drawing-substitute graph showing an example in which, for data of the dielectric constant of blood measured over time, the method of Embodiment 5 is used to evaluate the blood condition.

(e) Embodiment 5 a. First, as shown in FIG. 12, the first value and the last value are connected by a straight line.

b. Next, the difference between the straight line mentioned above and the original data is found at each time.

c. It can be evaluated that the time at which the difference found is at the maximum is the end time of coagulation of blood and the time at which the difference found is at the minimum is the start time of coagulation of blood.

In Embodiment 5, not limited to this method, it is also possible to use known similar methods.

In the extraction method and the blood condition evaluation method of Embodiments 1 to 5 described above, temporal change data in the total time are used for the electrical characteristics of blood; but in the present technology, it is also possible to perform fitting only in an early time, or to predict a distinctive time from data up to a time exceeding an arbitrary threshold or from the slope, position, etc. after the first change point of a linear function.

(4) Extraction Criterion Setting Unit 4

In the extraction criterion setting unit 4, the extraction criterion in the extraction unit 2 is set. In the blood condition analyzing device 1 according to the present technology, the extraction criterion setting unit 4 is not essential, but is preferably included in order to improve analysis precision more.

In the extraction criterion setting unit 4, for example, it is possible to set which extraction method to use out of Embodiments 1 to 5 of the extraction method described above, and to set a detailed criterion in each extraction method.

(5) Measuring Unit 7

In the measuring unit 7, the electrical characteristics of blood at an arbitrary frequency are measured over time. In the blood condition analyzing device 1 according to the present technology, the measuring unit 7 is not essential, and it is also possible to use data measured using an external electrical characteristic measuring device.

The measuring unit 7 may include one or a plurality of blood sample holding units. In the blood condition analyzing device 1, the blood sample holding unit is not essential, and the measuring unit 7 may be designed to be a configuration in which a known cartridge-type container for measurement or the like can be installed, for example.

In the case where the measuring unit 7 includes a blood sample holding unit, the configuration of the blood sample holding unit is not particularly limited to the extent that the blood sample of the measuring object can be held in the measuring unit 7, and may be designed to be an arbitrary configuration. For example, one or a plurality of cells provided on a substrate may be allowed to function as the blood sample holding unit, or one or a plurality of containers may be allowed to function as the blood sample holding unit.

In the case where one or a plurality of containers are used as the blood sample holding unit, the configuration of the container is not particularly limited, and may be freely designed in accordance with the condition, measuring method, etc. of the blood sample to the extent that the blood sample of the measuring object can be held, including a circular cylindrical body, a polygonal cylindrical body with a polygonal cross section (triangle, quadrangle, or polygon with more angles), a conical body, a polygonal pyramid-like body with a polygonal cross section (triangle, quadrangle, or polygon with more angles), or a configuration in which one or more of these are combined.

Also the material that forms the container is not particularly limited, and may be freely selected to the extent that there is no influence on the condition, measurement objective, etc. of the blood sample of the measuring object. In the present technology, in particular, the container is preferably formed using a resin from the viewpoint of the ease of processing and molding etc. In the present technology, also the type of usable resin is not particularly limited, and one or more types of resin usable for the holding of the blood sample may be freely selected for use. For example, a hydrophobic and insulating polymer such as polypropylene, poly(methyl methacrylate), polystyrene, an acrylic, a polysulfone, and polytetrafluoroethylene, a copolymer and a blend polymer thereof, and the like are given. In the present technology, the blood sample holding unit is preferably formed of, among the above materials, particularly one or more types of resin selected from polypropylene, polystyrene, an acrylic, and a polysulfone, because these resins have the property of being low coagulation-active against blood.

The blood sample holding unit is preferably in a configuration capable of being sealed in the state of holding the blood sample. However, the blood sample holding unit may not be in an airtight configuration to the extent that it is capable of being stationary through the time expected to measure the electrical characteristics of the blood sample and there is no influence on measurement.

Specific methods for introducing the blood sample into the blood sample holding unit and for making sealing are not particularly limited, and the introduction may be made by an arbitrary method in accordance with the configuration of the blood sample holding unit. For example, although not shown in the drawings, a method in which the blood sample holding unit is provided with a lid, and a blood sample is introduced using a pipette or the like and then the lid is closed to make sealing, a method in which the blood sample holding unit is pierced with a needle from its outer surface, and a blood sample is injected and then the portion pierced with the needle is sealed with grease or the like to make sealing, etc. are given.

The measuring unit 7 may include one or a plurality of applying units. In the blood condition analyzing device 1, the applying unit is not essential, and it is also possible to use an external applying unit by, for example, designing so that an electrode can be inserted into the blood sample holding unit from the outside.

The applying unit applies a prescribed voltage to the blood sample at each set measuring interval from, as the starting time point, the time point at which an order to start measurement is received or the time point at which the power supply for the blood condition analyzing device 1 is set to ON.

The number of electrodes used as part of the applying unit and the material that forms the electrode are not particularly limited to the extent that the effect of the present technology is not impaired, and it is possible to form an arbitrary number of electrodes using an arbitrary material. For example, titanium, aluminum, stainless steel, platinum, gold, copper, graphite, and the like are given. In the present technology, the electrodes are preferably formed of, among the above materials, particularly an electrically conductive material containing titanium, because titanium has the property of being low coagulation-active against blood.

In the measuring unit 7, it is also possible to perform a plurality of measurements. As the method for performing a plurality of measurements, for example, a method in which a plurality of measurements are performed simultaneously by a plurality of measuring units 7 being provided, a method in which a plurality of measurements are performed by scanning one measuring unit 7, a method in which a plurality of measurements are performed by moving the blood sample holding unit, a method in which a plurality of measuring units 7 are provided and switching is performed to select one or a plurality of measuring units 7 that actually perform measurement, etc. may be given.

In the measuring unit 7, the frequency band in which electrical measurement is performed may be appropriately selected in accordance with the condition, measurement objective, etc. of the blood to be measured. For example, when the electrical characteristic of the blood to be measured is impedance, a change is seen in the frequency bands shown in Table 3 below in accordance with the condition change of the blood.

TABLE 3

| | Impedance | |
| --- | --- | --- |
| Condition change of blood | Frequency at which change is seen | Frequency at which change is more significant |
| Coagulation of blood (blood coagulation) | 1 kHz to 50 MHz | 3 MHz to 15 MHz |
| Fibrin formation | 1 kHz to 50 MHz | 3 MHz to 15 MHz |
| Fibrin clot formation | 1 kHz to 50 MHz | 3 MHz to 15 MHz |
| Blood clot formation | 1 kHz to 50 MHz | 3 MHz to 15 MHz |
| Rouleaux formation of red blood cells | 500 kHz to 25 MHz | 2 MHz to 10 MHz |
| Aggregation of blood | 1 kHz to 50 MHz | 500 kHz to 5 MHz |
| Sedimentation of red blood cells (erythrocyte sedimentation) | 1 kHz to 50 MHz | 100 kHz to 40 MHz |
| Blood clot retraction (retraction) | 1 kHz to 50 MHz | 10 kHz to 100 kHz |
| Hemolysis | 1 kHz to 50 MHz | 3 MHz to 15 MHz |
| Fibrinolysis | 1 kHz to 50 MHz | 3 MHz to 15 MHz |

For example, in the case where the objective is to predict or detect the coagulation of blood (blood coagulation), it is preferable to measure the impedance at frequencies of 1 kHz to 50 MHz, and it is more preferable to measure the impedance at frequencies of 3 MHz to 15 MHz. By setting a parameter in accordance with the condition or measurement objective of blood beforehand in this way, a preferable frequency band like those shown in Table 3 above can be automatically selected.

(6) Storage Unit 8

The blood condition analyzing device 1 according to the present technology may include an extraction result storage unit 81 that stores the extraction results in the extraction unit 2, a blood condition evaluation storage unit 82 that stores the evaluation results in the blood condition evaluation unit 3, and a measurement result storage unit 83 that stores the measurement results in the measuring unit 7. In the blood condition analyzing device 1 according to the present technology, these storage units 8 are not essential, and the results may be stored by connecting an external storage device.

In the blood condition analyzing device 1 according to the present technology, the extraction result storage unit 81, the blood condition evaluation storage unit 82, and the measurement result storage unit 83 may each be provided separately, or it is also possible to design so that one storage unit 8 functions as the extraction result storage unit 81, the blood condition evaluation storage unit 82, and the measurement result storage unit 83.

(7) Blood Sample

In the blood condition analyzing device 1 according to the present technology, the blood sample that can be the measuring object is not particularly limited to the extent that it is a sample containing blood, and may be freely selected. Specific examples of the blood sample include a sample containing a blood component such as whole blood, blood plasma, or a diluted solution and/or a drug-added substance thereof, etc.

2. Blood Condition Analyzing System 10

Figure 13:
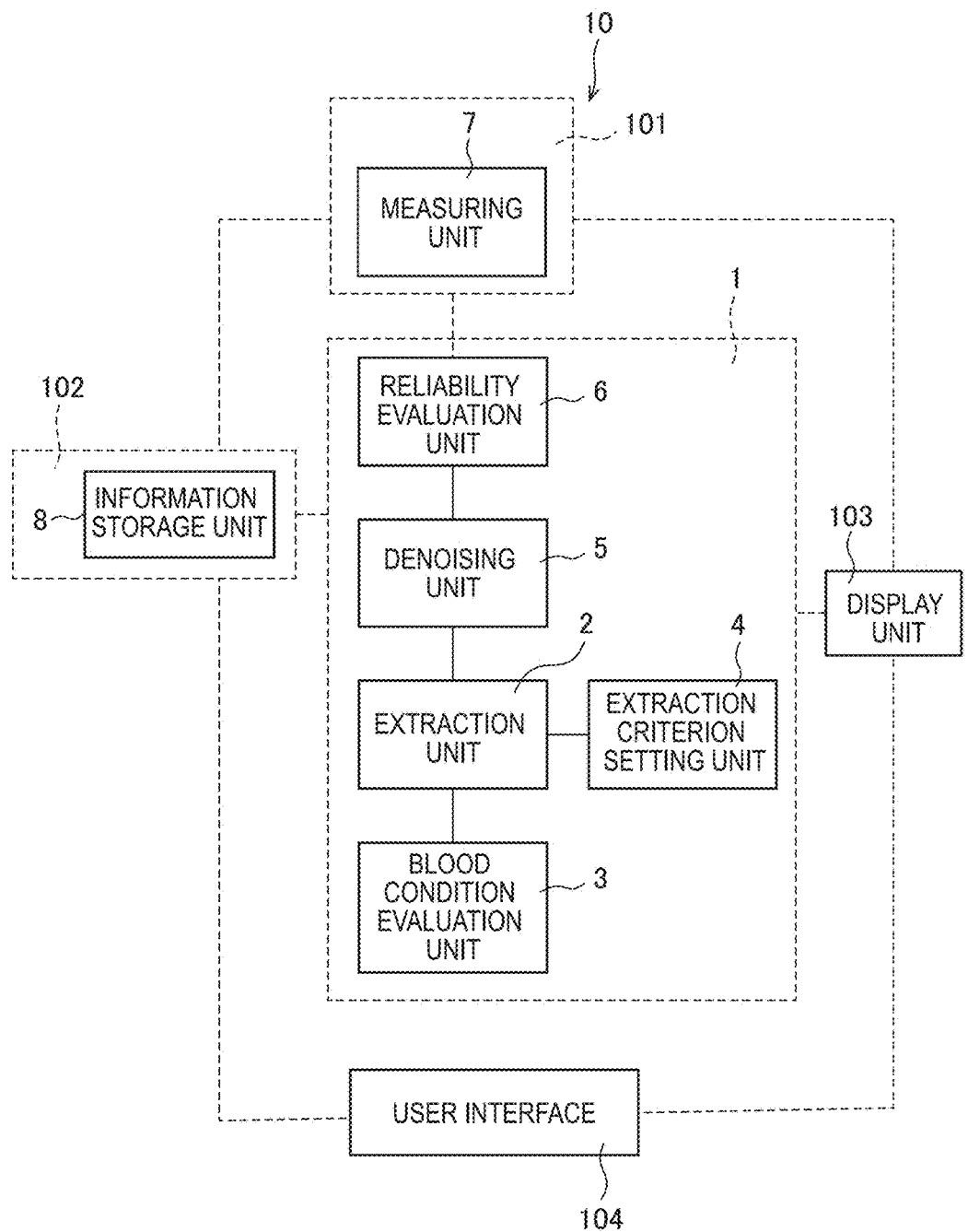
FIG. 13 is a schematic conceptual diagram schematically showing the concept of a blood condition analyzing system 10 according to the present technology.

FIG. 13 is a schematic conceptual diagram schematically showing the concept of a blood condition analyzing system 10 according to the present technology. The blood condition analyzing system 10 according to the present technology includes, in terms of broad categories, at least an electrical characteristic measuring device 101 and the blood condition analyzing device 1. The blood condition analyzing system 10 may include, as necessary, a server 102, a display unit 103, a user interface 104, etc. Each component will now be described in detail.

(1) Electrical Characteristic Measuring Device 101

The electrical characteristic measuring device 101 includes the measuring unit 7 that measures the electrical characteristics of blood at an arbitrary frequency over time. The details of the measuring unit 7 are the same as those of the measuring unit 7 in the blood condition analyzing device 1 described above.

(2) Blood Condition Analyzing Device 1

The blood condition analyzing device 1 includes, in terms of broad categories, at least the extraction unit 2 and the blood condition evaluation unit 3. The blood condition analyzing device 1 may include, as necessary, the extraction criterion setting unit 4, the denoising unit 5, the reliability evaluation unit 6, etc. Each component included in the blood condition analyzing device 1 is the same as the details of the blood condition analyzing device 1 described above.

(3) Server 102

The server 102 includes an information storage unit 8 that stores the measurement results in the electrical characteristic measuring device 101 and/or the analysis results in the blood condition analyzing device 1. The details of the information storage unit 8 are the same as those of the storage unit 8 in the blood condition analyzing device 1 described above.

(4) Display Unit 103

On the display unit 103, the temporal change data of electrical characteristics measured in the measuring unit 7, data in which noise is removed from the temporal change data, data in which a feature is extracted by the extraction unit 2, the blood condition evaluation results obtained by the blood condition evaluation unit 3, etc. are displayed. It is possible to provide a plurality of display units 103 individually for data or results to be displayed, or to display all data or results on one display unit 103.

(5) User Interface 104

The user interface 104 is a part for a user's operation. A user can access each part of the blood condition analyzing system 10 according to the present technology through the user interface 104.

In the blood condition analyzing system 10 according to the present technology described above, the electrical characteristic measuring device 101, the blood condition analyzing device 1, the server 102, the display unit 103, and the user interface 104 may be connected to each other via a network.

3. Blood Condition Analyzing Method

Figure 14:
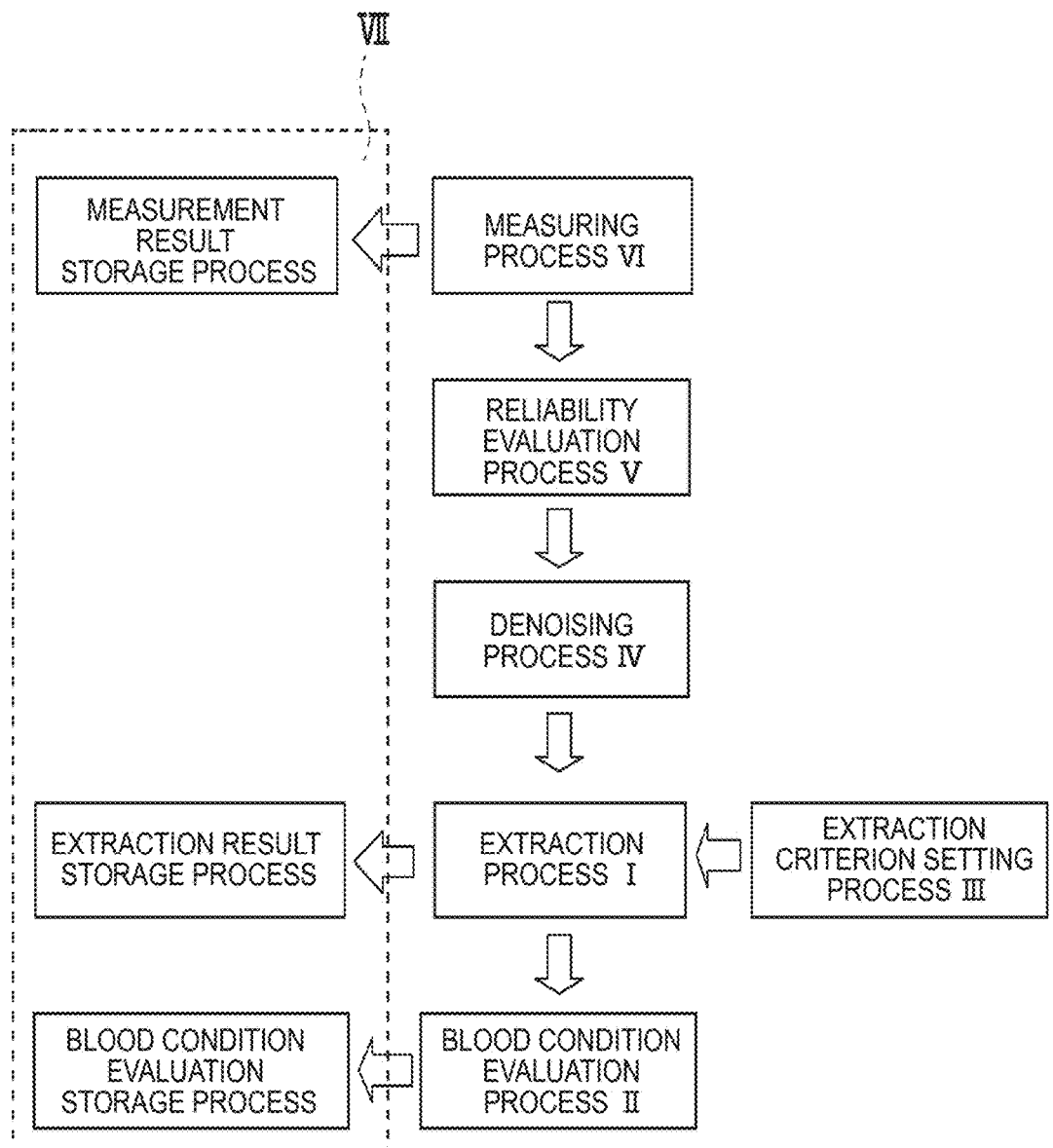
FIG. 14 is a flow chart of a blood condition analyzing method according to the present technology.

FIG. 14 is a flow chart of a blood condition analyzing method according to the present technology. In the blood condition analyzing method according to the present technology, an extraction process I and a blood condition evaluation process II are performed. It is also possible to perform an extraction criterion setting process III, a denoising process IV, a reliability evaluation process V, a measuring process VI, a storage process VII, etc., as necessary. Each process will now be described in detail.

(1) Extraction Process I

In the extraction process I, the temporal change data of the electrical characteristics of blood at an arbitrary frequency are used to extract a feature of the data. The details of the extraction method performed in the extraction process I are the same as those of the extraction method performed in the extraction unit 2 of the blood condition analyzing device 1 described above.

(2) Blood Condition Evaluation Process II

In the blood condition evaluation process II, the condition change of blood is evaluated from the feature extracted in the extraction process I. The details of the evaluation method performed in the blood condition evaluation process II are the same as those of the evaluation method performed in the blood condition evaluation unit 3 of the blood condition analyzing device 1 described above.

(3) Extraction Criterion Setting process III

In the extraction criterion setting process III, the extraction criterion in the extraction process I is set. In the blood condition analyzing method according to the present technology, the extraction criterion setting process III is not an essential process, but is preferably performed in order to improve analysis precision more. The details of the setting method performed in the extraction criterion setting process III are the same as those of the setting method performed in the extraction criterion setting unit 4 of the blood condition analyzing device 1 described above.

(4) Denoising Process IV

In the denoising process IV, the noise of the temporal change data of electrical characteristics is removed. In the blood condition analyzing method according to the present technology, the denoising process IV is not an essential process, but is preferably performed in order to improve analysis precision more. The details of the denoising method performed in the denoising process IV are the same as those of the denoising method performed in the denoising unit 5 of the blood condition analyzing device 1 described above.

(5) Reliability Evaluation Process V

In the reliability evaluation process V, the reliability of the temporal change data of electrical characteristics is evaluated. In the blood condition analyzing method according to the present technology, the reliability evaluation process V is not an essential process, but is preferably performed in order to improve analysis precision more. The details of the reliability evaluation method performed in the reliability evaluation process V are the same as those of the reliability evaluation method performed in the reliability evaluation unit 6 of the blood condition analyzing device 1 described above.

(6) Measuring Process VI

In the measuring process VI, the electrical characteristics of blood at an arbitrary frequency are measured over time. In the blood condition analyzing method according to the present technology, the measuring process VI is not an essential process, and it is also possible to perform analysis using data measured beforehand. The details of the measuring method performed in the measuring process VI are the same as those of the measuring method performed in the measuring unit 7 of the blood condition analyzing device 1 described above.

(7) Storage Process VII

In the blood condition analyzing method according to the present technology, storage processes VII such as an extraction result storage process that stores the extraction results extracted in the extraction process I, a blood condition evaluation storage process that stores the evaluation results evaluated in the blood condition evaluation process II, and a measurement result storage process that stores the measurement results measured in the measuring process VI may be performed. In the blood condition analyzing method according to the present technology, these storage processes VII are not essential, but are preferably performed in order to facilitate performing re-analysis etc.

4. Blood Condition Analyzing Program

A blood condition analyzing program according to the present technology is a program for causing a computer to execute an extraction function and a blood condition evaluation function. It is also possible to cause a computer to execute an extraction criterion setting function, a denoising function, a reliability evaluation function, etc., as necessary.

In other words, the blood condition analyzing program according to the present technology is a program for causing a computer to execute the blood condition analyzing method according to the present technology described above. Thus, the details of each function are the same as those of each process of the blood condition analyzing method described above, and a description is omitted herein.

Additionally, the present technology may also be configured as below.

(1)

A blood condition analyzing device including:
 an extraction unit configured to use temporal change data of an electrical characteristic of blood at an arbitrary frequency to extract a feature of the data; and
 a blood condition evaluation unit configured to evaluate a condition change of blood from a feature extracted in the extraction unit.

(2)

The blood condition analyzing device according to (1), further including:
 an extraction criterion setting unit configured to set an extraction criterion in the extraction unit.

(3)

The blood condition analyzing device according to (1) or (2), further including: a denoising unit configured to remove noise of the temporal change data of the electrical characteristic.

(4)

The blood condition analyzing device according to any one of (1) to (3), further including:
 a reliability evaluation unit configured to evaluate reliability of the temporal change data of the electrical characteristic.

(5)

The blood condition analyzing device according to any one of (1) to (4), further including:
a measuring unit configured to measure an electrical characteristic of blood at an arbitrary frequency over time.

(6)

The blood condition analyzing device according to any one of (1) to (5), further including:
an extraction result storage unit configured to store an extraction result in the extraction unit.

(7)

The blood condition analyzing device according to any one of (1) to (6), further including:
a blood condition evaluation storage unit configured to store an evaluation result in the blood condition evaluation unit.

(8)

The blood condition analyzing device according to (5), further including: a measurement result storage unit configured to store a measurement result in the measuring unit.

(9)

A blood condition analyzing system including:
an electrical characteristic measuring device including a measuring unit configured to measure an electrical characteristic of blood at an arbitrary frequency over time; and
a blood condition analyzing device including
an extraction unit configured to use temporal change data of an electrical characteristic of blood at an arbitrary frequency to extract a feature of the data and
a blood condition evaluation unit configured to evaluate a condition change of blood from a feature extracted in the extraction unit.

(10)

The blood condition analyzing system according to (9), further including:
a server including an information storage unit configured to store a measurement result in the electrical characteristic measuring device and/or an analysis result in the blood condition analyzing device.

(11)

The blood condition analyzing system according to (10), wherein the server is connected to the electrical characteristic measuring device and/or the blood condition analyzing device via a network.

(12)

A blood condition analyzing method for performing:
an extraction process of using temporal change data of an electrical characteristic of blood at an arbitrary frequency to extract a feature of the data; and
a blood condition evaluation process of evaluating a condition change of blood from a feature extracted in the extraction process.

(13)

A blood condition analyzing program for causing a computer to execute:
an extraction function of using temporal change data of an electrical characteristic of blood at an arbitrary frequency to extract a feature of the data; and
a blood condition evaluation function of evaluating a condition change of blood from a feature extracted in the extraction function.

The effects described in the present specification are only examples and not limitative ones; and there may be other effects.

REFERENCE SIGNS LIST 1 blood condition analyzing device
6 reliability evaluation unit
5 denoising unit
2 extraction unit
3 blood condition evaluation unit
4 extraction criterion setting unit
7 measuring unit
8 storage unit
10 blood condition analyzing system
101 electrical characteristic measuring device
102 server
103 display unit
104 user interface
I extraction process
II blood condition evaluation process
III extraction criterion setting process
IV denoising process
V reliability evaluation process
VI measuring process
VII storage process

The invention claimed is:

1. A blood condition analyzing system comprising:
an electrical characteristic measuring device including at least one electrode configured to be arranged in electrical contact with a blood sample, the electrical characteristic measuring device configured to:
apply a voltage to the at least one electrode;
select a frequency band for measuring an electrical characteristic of the blood sample; and
measure the electrical characteristic of the blood sample at a plurality of time points and within the selected frequency band to generate temporal change data of the electrical characteristic of the blood sample;
a blood condition analyzing device configured to:
select an extraction method from a plurality of extraction methods for evaluating a blood condition;
analyze the temporal change data of the electrical characteristic of the blood sample to extract a feature of the data according to the selected extraction method; and
evaluate a condition change of the blood sample from the extracted feature according to the selected extraction method; and
a display configured to:
display an indication of the blood condition based on the evaluation of the condition change of the blood sample to facilitate a diagnosis.

2. The blood condition analyzing system according to claim 1, wherein the blood condition analyzing device is further configured to set an extraction criterion used to extract the feature of the data.

3. The blood condition analyzing system according to claim 1, wherein the blood condition analyzing device is further configured to remove noise of the temporal change data of the electrical characteristic.

4. The blood condition analyzing system according to claim 1, wherein the blood condition analyzing device is further configured to evaluate reliability of the temporal change data of the electrical characteristic.

5. The blood condition analyzing system according to claim 1, wherein the blood condition analyzing device is further configured to store an extraction result.

6. The blood condition analyzing system according to claim 1, wherein the blood condition analyzing device is further configured to store an evaluation result.

7. The blood condition analyzing system according to claim 1, wherein the blood condition analyzing device is further configured to store a measurement result.

8. The blood condition analyzing system according to claim 1, further comprising:
a server configured to store a measurement result in the electrical characteristic measuring device and/or an analysis result in the blood condition analyzing device.

9. The blood condition analyzing system according to claim 8, wherein the server is connected to the electrical characteristic measuring device and/or the blood condition analyzing device via a network.

10. A non-transitory computer-readable storage medium storing a blood condition analyzing program for causing a computer to execute:
applying a voltage to at least one electrode configured to be arranged in electrical contact with a blood sample;
selecting a frequency band for measuring an electrical characteristic of the blood sample;
measuring the electrical characteristic of the blood sample at a plurality of time points and within the selected frequency band to generate temporal change data of the electrical characteristic of the blood sample;
selecting an extraction method from a plurality of extraction methods for evaluating a blood condition;
analyzing the temporal change data of the electrical characteristic of the blood sample to extract a feature of the data according to the selected extraction method;
evaluating a condition change of the blood sample from the extracted feature according to the selected extraction method; and
displaying an indication of the blood condition based on the evaluation of the condition change of the blood sample to facilitate a diagnosis.

11. The blood condition analyzing system according to claim 1,
wherein analyzing temporal change data according to the selected extraction method comprises:
determining an average amplitude M of a minimum value and a maximum value of the temporal change data;
connecting each datum in the temporal change data from a point (1, M) to obtain a plurality of line segments; and
determining a line segment with a maximum slope, and
wherein evaluating a condition change of the blood sample according to the selected extraction method comprises:
evaluating an end of blood coagulation based on a datum corresponding to the line segment.

12. The blood condition analyzing system according to claim 1,
wherein analyzing temporal change data according to the selected extraction method comprises:
determining an average amplitude M of a minimum value and a maximum value of the data;
connecting each datum in the data corresponding to a time less than T from a point (T, M) to obtain a plurality of line segments; and
determining a line segment with a maximum slope, and
wherein evaluating a condition change of the blood sample according to the selected extraction method comprises:
evaluating a start of blood coagulation based on a datum corresponding to the line segment.

13. The blood condition analyzing system according to claim 1, wherein the electrical characteristic measuring device includes at least one blood sample holder configured to hold the blood sample, wherein the at least one blood sample holder comprises a substrate having at least one cell provided thereon or at least one container.

14. The blood condition analyzing system according to claim 1, wherein the plurality of extraction methods comprise a linear approximation method, a linear projection method, an approximation method using non-linear rational functions, and a boundary detection algorithm.

15. The blood condition analyzing system according to claim 1, wherein the selected frequency band is selected based, at least in part, on the blood condition being analyzed.

16. A method for analyzing a blood condition comprising:
applying a voltage to at least one electrode configured to be arranged in electrical contact with a blood sample;
selecting a frequency band for measuring an electrical characteristic of the blood sample;
measuring the electrical characteristic of the blood sample at a plurality of time points and within the selected frequency band to generate temporal change data of the electrical characteristic of the blood sample;
selecting an extraction method from a plurality of extraction methods for evaluating a blood condition;
analyzing the temporal change data of the electrical characteristic of the blood sample to extract a feature of the data according to the selected extraction method;
evaluating a condition change of the blood sample from the extracted feature according to the selected extraction method; and
displaying an indication of the blood condition based on the evaluation of the condition change of the blood sample to facilitate a diagnosis.

* * * * *